United States Patent [19]

Manchand et al.

[11] 4,218,567
[45] Aug. 19, 1980

[54] PROCESS FOR AROMATIC ETHERS

[75] Inventors: Percy S. Manchand; John M. Townsend, both of Montclair, N.J.

[73] Assignee: Hoffmann-La Roche Inc., Nutley, N.J.

[21] Appl. No.: 910,549

[22] Filed: May 30, 1978

[51] Int. Cl.$^2$ ............................................. C07C 69/76
[52] U.S. Cl. ..................... 562/475; 560/64; 560/65; 560/67; 560/77; 560/71; 560/103; 568/608; 568/433
[58] Field of Search ...................... 560/64, 65, 71, 67, 560/77, 103; 562/475; 260/599, 600 R; 568/608

[56] References Cited

PUBLICATIONS

March, J.; Advanced Organic Chemistry, pp. 482–483 and 357–358 2nd Ed., copyright 1968.

*Primary Examiner*—Paul J. Killos
*Attorney, Agent, or Firm*—Jon S. Saxe; George M. Gould; Peter R. Shearer

[57] ABSTRACT

A process for the preparation of aromatic ethers by the bromination of a compound of the formula

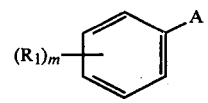

II wherein $R_1$, independently, is hydrogen, hydroxy, lower alkoxy, lower alkyl; m is an integer from 1–4, and A is —CHO, —COOR$_3$ or lower alkyl, and subsequently treating the reaction product of the bromination step with an alkali metal alkoxide in the presence of cuprous halide or oxide, is described.

6 Claims, No Drawings

PROCESS FOR AROMATIC ETHERS

BACKGROUND OF THE INVENTION

Aromatic aldehydes, acids and esters, particularly those substituted on the aromatic ring with ether groups, are important compounds in the perfume industry, and also serve as precursors for the manufacture of pharmaceuticals. Previous methods for preparing the foregoing aromatic aldehydes, acids and esters involved either methylating phenolic aldehydes or introducing an aldehyde group into a preformed aromatic ether.

In a series of papers, Bacon and S. C. Rennison [J. Chem. Soc., (C), 308, 213, 1978 (1969)] reported that aromatic halides when treated with sodium methoxide in the presence of cuprous salts, notably cuprous iodide, produced aromatic ethers. The authors further reported, see page 312, that aromatic bromides bearing phenolic and/or aldehydic groups gave poor yields, that is, 36–46% of the corresponding ethers in the reaction. By the present invention, it has now been unexpectedly found that aromatic ethers bearing aldehyde and/or phenol groups, as well as acid and ester groups, can be prepared in excellent yields, that is, 85–95%, by treating the corresponding aromatic bromides with, for example, sodium methoxide in dimethylformamide in the presence of cuprous chloride as catalyst.

BRIEF SUMMARY OF THE INVENTION

A process for adding one or more ether groups to obtain a compound characterized by the formula

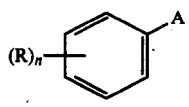

wherein A is —CHO, —COOR$_3$ or lower alkyl, wherein R$_3$ is H or lower alkyl; R, independently, is hydroxy, lower alkoxy or lower alkyl, and n is an integer from 1 to 5, provided that at least one R is lower alkoxy, which comprises brominating a compound of the formula

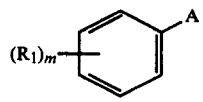

wherein R$_1$, independently, is hydrogen, hydroxy, lower alkoxy or lower alkyl; m is an integer from 1 to 4, and A is as previously described, and subsequently treating the reaction product of the bromination step with an alkali metal alkoxide in the presence of cuprous halide or oxide to obtain the desired end product of formula I.

DETAILED DESCRIPTION OF THE INVENTION

The invention relates to a process for preparing compounds characterized by the formula

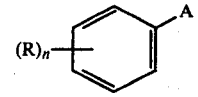

wherein A is —CHO, —COOR$_3$ or lower alkyl, wherein R$_3$ is H or lower alkyl; R, independently, is hydroxy, lower alkoxy or lower alkyl, and n is an integer from 1 to 5, provided that at least one R is lower alkoxy.

The compounds of formula I are prepared by bromination of a compound of the formula

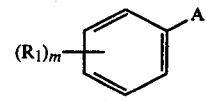

wherein R$_1$, independently, is hydrogen, hydroxy, lower alkoxy or lower alkyl; m is an integer from 1 to 4, and A is as previously described.

The bromination can be carried out with or without solvents. Suitable solvents comprise alkanols, such as methanol, hydrocarbons, such as toluene, or the like. Bromination is carried out at room temperature or below. The brominating agents which can be utilized comprise bromine, dioxan-dibromide, or the like. If desired, catalysts, for example, a Lewis acid, such as aluminum chloride, may be utilized in the bromination step. The reaction is carried out at atmospheric pressure.

There is formed, as an intermediate, a compound of the formula

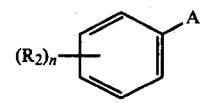

wherein R$_2$, independently, is hydroxy, lower alkoxy, lower alkyl or bromine, provided that at least one R$_2$ is bromo; n is an integer of from 1 to 5; and A is as previously described, which can be recovered according to known procedures or can be utilized in situ in the next reaction step. The compound of formula III is converted to a compound of formula I utilizing an alkali metal alkoxide, such as sodium alkoxide or potassium alkoxide in the presence of cuprous halide or oxide. The reaction is preferably carried out at a temperature in the range of 40° to about 160°, at atmospheric pressure. The reaction is carried out in the presence of a solvent, for example, pyridine, dimethylformamide, collidine, or the like. Optionally, the reaction may be carried out in a mixture comprising a solvent referred to above and an alkanol, such as, methanol, ethanol, or the like.

The desired compound of formula I which is formed can be recovered utilizing conventional procedures, such as crystallization or the like. The compounds of formula I are known compounds and can be utilized as intermediates for the preparation of known pharmaceutical compounds, as well as being useful in the perfume industry.

Exemplary of the substituted aromatic compounds of formula I which can be prepared by the process of the invention are:

3,4,5-trimethoxybenzaldehyde,
3,4,5-trimethoxybenzoic acid,
3,4-dimethoxytoluene,
3,5-dimethoxy-4-methylbenzoic acid,
the methyl ester of 3,4,5-trimethoxybenzoic acid,
3,4-dimethoxybenzaldehyde, and the like.
Exemplary of the compounds of formula II are:
3-methoxy-4-hydroxybenzaldehyde,
4-hydroxybenzaldehyde,
4-hydroxytoluene;
4-hydroxybenzoic acid; and
the methyl ester of 4-methylbenzoic acid.

The following Examples further illustrate the invention. All temperatures are stated in degrees Centigrade, unless otherwise mentioned.

EXAMPLE 1

Preparation of 3,5-dibromo-4-hydroxybenzaldehyde

A 2-l., 3-necked round-bottomed flask equipped with a condenser attached to a calcium sulfate drying tower, mechanical stirrer, thermometer, and dropping funnel was charged with a solution of 108.1 g. of p-cresol (99%) in 500 ml. of chlorobenzene (anhydrous). The solution was cooled to 10° and treated during 30 minutes with a solution of 720 g. of bromine in 600 ml. of chlorobenzene at such a rate that the temperature was kept below 25°. The mixture was stirred at room temperature for 30 minutes, heated under reflux for 4.5 hours, and then evaporated in vacuo (water aspirator) at 60° to give a deep red oil which was dissolved in 1.0 l. of methanol. To the stirred, cooled (10°) solution was added 500 ml. of 1 N hydrochloric acid at such a rate that the temperature was kept below 25°. The mixture was left at 5° overnight, diluted with 1.0 l. of cold (5°) water and the product collected by filtration. The solid was washed with four 1-l. portions, a total of 4.0 l. of water, dissolved in 2.5 l. of warm (50°) ethyl acetate, dried over magnesium sulfate, and evaporated to give 291 g. of an off-white solid. To the solid was added 600 ml. of methylene chloride and the heterogeneous mixture heated at reflux for 15 minutes, diluted with 600 ml. of hexane and left at 0° overnight. The off-white solid was collected, washed with two 100 ml. portions, a total of 200 ml. of cold (5°) hexane, and dried in vacuo at room temperature overnight to give 168.3 g. (60%) of 3,5-dibromo-4-hydroxybenzaldehyde as a colorless solid, mp 177°–180°. GLC analysis indicated a purity of 99.6%.

EXAMPLE 2

Preparation of 3,5-dimethoxy-4-hydroxybenzaldehyde

Into a 2-l., 3-necked, round-bottomed flask equipped with a mechanical stirrer, thermometer, and a condenser was added 700 ml. of methanol. 68.0 G. of clean sodium was then added in small pieces and under nitrogen. After the reaction was complete, the methanol was removed in vacuo at 45°–50° and to the residue was added 312 ml. of dimethylformamide and 156 ml. of methanol. 5.85 G. of cuprous chloride was added followed, after 5 minutes, by 165 g. of 3,5-dibromo-4-hydroxybenzaldehyde, an exotherm resulted (25° to 50° during 5 minutes). The mixture was heated under reflux for 4 hours, the solvents were evaporated in vacuo (0.1 torr) at 55°, and the residue was treated with 440 ml. of 15% brine. The mixture was stirred at room temperature for 30 minutes, again cooled to 0°, and filtered over 100 g. of celite. The filter cake was washed with three 250 ml. portions, a total of 750 ml. of cold (5°) water (that is, until neutral) followed, after discarding the aqueous washings, by three 500 ml. portions, a total of 1.5 l. of hot (60°) ethyl acetate. The ethyl acetate washings were added to a separatory funnel, excess water (about 10 ml.) was removed, and the ethyl acetate dried over magnesium sulfate and evaporated to give 95.0 g. (88.5%) of 3,5-dimethoxy-4-hydroxybenzaldehyde as a yellow solid, mp 107°–109°. GLC indicated a purity of 99.7%.

EXAMPLE 3

Bromination of 3-methoxy-4-hydroxybenzaldehyde

A 3-l., 3-necked, round-bottomed flask equipped with a mechanical stirrer, condenser capped with a Drierite drying tube, thermometer and addition funnel was charged with a solution of 152.15 g. of 3-methoxy-4-hydroxybenzaldehyde in 1.0 l. of methanol. The stirred solution was cooled to 0° and treated dropwise with 176.0 g. of bromine at such a rate that the temperature of the reaction was kept below 20°; the addition time was 20 minutes. The mixture was stirred at room temperature for 1 hour, cooled to 0° and treated dropwise during 30 minutes with 500 ml. of cold (5°) water. The crystals were stirred at 5° for 15 minutes, collected by filtration, washed with four 500 ml. portions, a total of 2.0 l. of water, and then with 500 ml. of cold (0°) 70% methanol. The product was dried in vacuo at 70° overnight to give 218.5 g. (95%) of 3-methoxy-4-hydroxy-5-bromobenzaldehyde as pale yellow crystals, mp 163°–164°; estimated purity of 99.68%.

EXAMPLE 4

Preparation of 3,5-dimethoxy-4-hydroxybenzaldehyde

Into a 5-l., 3-necked, round-bottomed flask equipped with a mechanical stirrer, thermometer, and condenser was added 1.0 l. of methanol. 85.2 G. of clean sodium was then added in small pieces and under nitrogen. After the reaction was complete, the methanol was removed at 45°–50° and 450 ml. of dimethylformamide added to the residue. To the rapidly stirred slurry of sodium methoxide in dimethylformamide was added 10.7 g. of cuprous chloride to give a deep blue mixture which was stirred at 25° for 15 minutes. 214.4 G. of 3-methoxy-4-hydroxy-5-bromobenzaldehyde was added during 3 minutes, whereupon a slight exotherm ensued. The temperature of the reaction was increased to 97° during 15 minutes and the mixture was stirred at this temperature for 1.75 hours. The reaction was cooled to 60° and the dimethylformamide distilled off under high vacuum. 1.0 l. of 15% brine was added to the residue, the mixture was stirred at 50° for 30 minutes, cooled to 0° and treated with 300 ml. of cold (0°) concentrated hydrochloric acid at such a rate that the temperature was kept below 15°. The mixture was stirred at room temperature for 1 hour, again cooled to 0° and filtered over 100 g. of celite. The filter cake was washed with four 400 ml. portions, a total of 1.6 l. of cold (5°) water, followed, after discarding the aqueous wash, by five 500 ml. portions, a total of 2.5 l. of hot (60°) ethyl acetate. The ethyl acetate washings were added to a separatory funnel, excess water (about 15 ml.) was ran off, and the ethyl acetate dried over magnesium sulfate and evaporated in vacuo to give 154.0 g. (91%) of 3,5-dimethoxy-4-hydroxybenzaldehyde as yellow crystals, mp 109°–111°, purity of 99.72%.

EXAMPLE 5

Preparation of the methyl ester of 3,5-dibromo-4-hydroxybenzoic acid

A 5-l., 3-necked, round-bottomed flask equipped with a mechanical stirrer, condenser capped with a drying tube, and thermometer was charged with 138.1 g. of 4-hydroxybenzoic acid and 1.0 l. of methanol. The mixture was stirred at room temperature for 5 minutes and treated with 328 g. of bromine during 20 minutes. The temperature of the reaction rose from 23° to 52° during the addition. The mixture was boiled under reflux with stirring for 4.0 hours. The heating source was removed, and stirring was continued for about 30 minutes until crystallization commenced. The mixture was stirred at room temperature for 20 minutes and then at 10° for an additional 20 minutes. 2.0 l. of water was added during 10 minutes, and the mixture was stirred at 20° for 30 minutes. The crystals were collected by filtration, washed with three 1-l. portions, a total of 3.0 l. of water, and then dissolved in 3.5 l. of hot (65°) ethyl acetate. The ethyl acetate solution was dried over magnesium sulfate and evaporated to give 308.7 g. (99.5%) of crude methyl 3,5-dibromo-4-hydroxybenzoate as a virtually colorless crystalline mass, mp 120°–121°, with an estimated purity of 99%.

EXAMPLE 6

Preparation of the methyl ester of 3,5-dimethoxy-4-hydroxybenzoic acid

A 5-l., 3-necked, round-bottomed flask equipped with a mechanical stirrer, condenser capped with a drying tube, and thermometer was charged with 1.37 l. of methanol followed by 137.0 g. of clean sodium in small pieces. When all the sodium had reacted, the methanol was removed completely and 29.5 g. of cuprous chloride was added. 308.0 G. of the methyl ester of 3,5-dibromo-4-hydroxybenzoic acid in 1.0 l. of dimethylformamide was added; the mixture was stirred at 90°–95° overnight (20 hours), and then evaporated in vacuo at 60°. 500 Ml. of methanol was added to the residue, the mixture was stirred at room temperature for 15 minutes, cooled to 5°, and treated with a solution of gaseous hydrogen chloride (160 g.) in 400 ml. of methanol during 30 minutes at a rate such that the temperature was kept below 15°. The methanol was removed in vacuo at 45°, 2.0 l. of ethyl acetate was added to the residue, followed by 50 g. of celite. The heterogeneous mixture was boiled under reflux with stirring for 10 minutes, and then filtered hot over 100 g. of celite (a 3-l. filter funnel with coarse porosity is recommended). The filter cake was washed with 1.0 l. of hot (65°) ethyl acetate, and the washing combined with the filtrate. The combined filtrate and washing (light purple) was washed with three 1-l. portions, a total of 3.0 l. of 20% brine. The aqueous phase was re-extracted with 500 ml. of ethyl acetate, washed with two 500 ml. portions, a total of 1.0 l. of 20% brine, and combined with the first extract. The combined ethyl acetate extracts were dried over magnesium sulfate, filtered, and evaporated to give 189 g. of crude methyl ester of 3,5-dimethoxy-4-hydroxybenzoic acid as an off-white solid, mp 92°–110°.

EXAMPLE 7

Preparation of 3,5-dibromo-4-hydroxybenzaldehyde

A 5-l., 3-necked, round-bottomed flask equipped with a mechanical stirrer, addition funnel, and thermometer was charged with 122.0 g. of 4-hydroxybenzaldehyde in 1.0 l. of methanol. The solution was cooled to 0° and treated dropwise with 325.0 g. of bromine at such a rate that the temperature of the reaction was kept below 20°; the addition time was 30 minutes. The mixture was stirred at room temperature for 1 hour, 800 ml. of methanol was removed by distillation at 50° (water aspirator), and to the warm (45°) solution was added 2.0 l. of water over a period of 20 minutes. The mixture was stirred at 0° for 1 hour and the product collected by filtration. The product was washed with five 1-l. portions, a total of 5 l. of water, then with 500 ml. of cold (0°) 70% methanol, and dried in vacuo (0.2 torr) at 70° for 18 hours to give 264.4 g. (95.5%) of 3,5-dibromo-4-hydroxybenzaldehyde as a colorless powder, mp 180°–183°.

EXAMPLE 8

Preparation of 3,5-dimethoxy-4-hydroxybenzaldehyde

A 5-l., 3-necked, round-bottomed flask equipped with a mechanical stirrer, condenser capped with a drying tube, and a thermometer was charged with 1.2 l. of methanol. 109.5 G. of clean sodium was then added in small pieces and under nitrogen. When all the sodium had reacted, the methanol was removed in vacuo at 50° and a mixture of 500 ml. of dimethylformamide and 250 ml. of methanol added to the residue. To the vigorously stirred solution was added 9.45 g. of cuprous chloride followed, after 5 minutes, by 264.4 g. of 3,5-dibromo-4-hydroxybenzaldehyde. An exotherm resulted in which the temperature rose from 23° to 50° over a period of 10 minutes. The mixture was stirred at 95° for 3.25 hours, during which time the color of the reaction changed from blue to greyish-green. The solvents were removed in vacuo at 45° and to the residue was added 700 ml. of 15% brine. The mixture was stirred at 60° for 30 minutes, cooled to 0° and treated with 400 ml. of cold (0°) concentrated hydrochloric acid at such a rate that the temperature was kept below 30°. The mixture was stirred at room temperature for 30 minutes, then at 0° for another 30 minutes, and filtered over 100 g. of celite. The filter cake was washed with four 400 ml. portions, a total of 1.6 l. of cold (5°) water, followed, after removing the aqueous washings, by four 500 ml. portions, a total of 2.0 l. of hot (60°) ethyl acetate. The ethyl acetate washings were added to a separatory funnel, excess water (about 20 ml.) was removed, and the ethyl acetate dried over magnesium sulfate and evaporated to give 153.3 g. (88%) of 3,5-dimethoxy-4-hydroxybenzaldehyde as a pale yellow solid, mp 105°–108°. Purity of 99.38%.

EXAMPLE 9

Preparation of 3-bromo-4-methoxytoluene

A 1-l. round-bottomed flask equipped with a mechanical stirrer and addition funnel was charged with a solution of 60 g. of sodium hydroxide in 300 ml. of water. To the stirred solution was added 108.0 g. of 4-hydroxytoluene followed by 126.1 g. of dimethylsulfate during 15 minutes. The mixture was stirred at 100° for 4 hours, cooled to room temperature, and then poured into a separatory funnel. The organic phase was collected, the aqueous phase was diluted with 200 ml. of water, and then extracted with 300 ml. of toluene. The extract and the organic material collected previously were combined, washed with three 100 ml. portions, a total of 300 ml., of water, and dried over magnesium sulfate. The mixture was filtered into a 1-l. round-bottomed flask equipped with a mechanical stirrer, addition funnel and thermometer. The solution was cooled to −10° and then treated with 168.0 g. of bromine at such a rate that the temperature was kept between −10° and 0°. The mixture was stirred at 0°—5° for 1 hour and then concentrated at 50° to give 210.2 g. of crude 3-bromo-4-methoxytoluene as an amber-colored oil. This material was used in the next step.

EXAMPLE 10

Preparation of 3,4-dimethoxytoluene

To a 3-l. round-bottomed flask equipped with a mechanical stirrer and condenser was added 1.2 l. of methanol followed by 138.0 g. of clean sodium in small pieces. After all the sodium had reacted, a solution of 210.2 g. of crude 3-bromo-4-methoxytoluene in 120 ml. of dimethylformamide was added, followed by 9.9 g. of freshly prepared cuprous chloride. The heterogeneous mixture was boiled under reflux for 4 hours and then stirred at room temperature overnight. The reaction mixture was poured into 1.21 l. of saturated brine. The solids were filtered off and the filter cake was washed with 500 ml. of hot (60%) toluene. This toluene wash was used to extract the filtrate. The filter cake was washed further with three 500 ml. portions, a total of 1.5 l. of hot (60°) toluene; each wash was used to back-extract the filtrate. The toluene washings were combined, washed with four 1-l. portions, a total of 4 l. of water, dried over magnesium sulfate and evaporated to give 153.0 g. of crude 3,4-dimethoxytoluene as a pale yellow oil which was distilled to give 125.9 g. of pure 3,4-dimethoxytoluene, bp (°)/mm 53—54/0.15.

EXAMPLE 11

Preparation of methyl 3,5-dibromo-4-methylbenzoate

213 G. of aluminum chloride was added, with stirring and cooling, to 90 g. of methyl 4-methylbenzoate followed by 223 g. of bromine during 30 minutes. Stirring was continued at room temperature for 30 minutes, and then at 80°—85° for 1 hour. The mixture was diluted with 1 l. of methanol and stirred at room temperature for 18 hours, and the product was collected by filtration. The product was washed with cold (10°) methanol (250 ml.), dissolved in 1 l. methylene chloride, and filtered through Celite. The filtrate was evaporated, and the residue was crystallized from 800 ml. methanol to give 118 g. of methyl 3,5-dibromo-4-methylbenzoate, mp 86°-88°.

EXAMPLE 12

Preparation of 3,5-dimethoxy-4-methylbenzoic acid

To a stirred solution of sodium methoxide (from 20.7 g. of sodium and 180 ml. of methanol) were added 46.2 g. of methyl 3,5-dibromo-4-methylbenzoate, 75 ml. of pyridine, and 2.12 g. of cuprous chloride. The mixture was boiled under reflux for 10 hours, cooled, and filtered through a pad of Celite. The filtrate was diluted with 100 ml. of water, and the mixture boiled under reflux for 1 hour. The mixture was cooled to room temperature, diluted with 300 ml. of brine, and extracted with 300 ml. of methylene chloride. The aqueous phase was acidified with 100 ml. of cold hydrochloric acid, extracted with 3×200 ml. of ethyl acetate, and the extract was washed with saturated brine, dried over magnesium sulfate, and evaporated to give 25.7 g. of crude 3,5-dimethoxy-4-methylbenzoic acid, mp 210°-216°.

EXAMPLE 13

Preparation of 3,5-dibromo-4-hydroxytoluene

To a cooled (0°) solution of 108 g. of p-cresol in 500 ml. of methanol was added 336 g. of bromine at such a rate that the internal temperature was kept below 10°. The mixture was stirred at room temperature for 2 hours, and then evaporated in vacuo. The residue was dissolved in a mixture of toluene in hexane (1:1) and left at −20° for 18 hours. The product was collected by filtration to give 252 g. of 3,5-dibromo-4-hydroxy-toluene, mp 46°-47°.

EXAMPLE 14

Preparation of 3,5-dimethoxy-4-hydroxytoluene

To a solution of freshly prepared sodium methoxide (from 12.4 g. of sodium and 75 ml. of methanol) was added 100 ml. of toluene and 4 ml. of pyridine. 1.114 G. of cuprous chloride and 23.94 g. of 3,5-dibromo-4-hydroxytoluene were then added. The mixture was boiled under reflux for 2 hours, cooled to room temperature, and acidified with 35 ml. concentrated hydrochloric acid. The mixture was filtered, the filtrate was extracted with methylene chloride (3×50 ml.), and the extract was washed with saturated brine, dried over magnesium sulfate and evaporated to give an oil. Distillation gave 13.61 g. (90%) of 3,5-dimethoxy-4-hydroxytoluene, bp 91°/0.2 mm.

We claim:

1. In a process for preparing a compound characterized by the formula

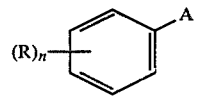

wherein A is —CHO or —COOR$_3$ or lower alkyl, wherein R$_3$ is H or lower alkyl; R, independently, is hydroxy, lower alkoxy or lower alkyl, and n is an integer from 1 to 5, provided that at least one R is lower alkoxy, wherein a compound of the formula

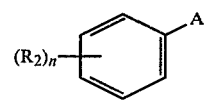

wherein R$_2$, independently, is hydroxy, lower alkoxy. lower alkyl or bromine, provided that at least one R$_2$ is bromo, and n and A are as previously described, is treated with an alkali metal alkoxide, the improvement which comprises carrying out the reaction in the presence of a catalytically effective amount of cuprous chloride.

2. A process as claimed in claim 1, wherein said reaction is carried out in dimethylformamide as a solvent.

3. A process as claimed in claim 1, wherein said compound of formula III is 3-methoxy-4-hydroxy-5-bromobenzaldehyde.

4. A process as claimed in claim 1, wherein said compound of formula III is 3,5-dibromo-4-hydroxybenzoic acid.

5. A process as claimed in claim 1, wherein said compound of formula III is 3,5-dibromo-4-hydroxybenzaldehyde.

6. A process as claimed in claim 1, wherein said compound of formula III is 3,5-dibromo-4-hydroxytoluene.